United States Patent [19]

Peck

[11] Patent Number: 5,648,167

[45] Date of Patent: Jul. 15, 1997

[54] ADHESIVE COMPOSITIONS

[75] Inventor: Roger Francis Peck, Stansted Mountfitchet, United Kingdom

[73] Assignee: Smith & Nephew PLC, England

[21] Appl. No.: 479,559

[22] Filed: Jun. 7, 1995

Related U.S. Application Data

[63] Continuation of Ser. No. 263,262, Jun. 21, 1994, abandoned, which is a continuation of Ser. No. 924,035, filed as PCT/GB91/00497, Mar. 28, 1991, abandoned.

[30] Foreign Application Priority Data

| Mar. 29, 1990 | [GB] | United Kingdom | 9007100 |
| Apr. 17, 1990 | [GB] | United Kingdom | 9008629 |
| Jun. 6, 1990 | [GB] | United Kingdom | 9012567 |

[51] Int. Cl.$^6$ .............................. B32B 7/10; A61F 13/00
[52] U.S. Cl. ........................... 428/355 AC; 428/212; 428/349; 428/131; 428/500; 428/520; 428/913; 602/54; 604/307; 442/151
[58] Field of Search ................................. 428/131, 200, 428/201, 261, 349, 355, 500, 515, 520, 913, 212; 156/327, 332; 602/54, 900; 604/307

[56] References Cited

U.S. PATENT DOCUMENTS

| 4,260,659 | 4/1981 | Gobran | 428/217 |
| 4,608,249 | 8/1986 | Otsuka et al. | 424/28 |
| 4,693,776 | 9/1987 | Krampe et al. | 156/327 |
| 4,880,683 | 11/1989 | Stow | 428/200 |
| 5,153,040 | 10/1992 | Faasse, Jr. | 428/40 |
| 5,156,911 | 10/1992 | Stewart | 428/355 |
| 5,387,450 | 2/1995 | Stewart | 428/40 |

FOREIGN PATENT DOCUMENTS 0062682  10/1982  European Pat. Off. .

*Primary Examiner*—Patrick Ryan
*Assistant Examiner*—Marie R. Yamnitzky
*Attorney, Agent, or Firm*—Graham & James LLP

[57] ABSTRACT

A medical adhesive product is provided comprising a substrate, a pressure sensitive adhesive on one face of the substrate and a layer of a polymer composition on the surface of the pressure sensitive adhesive wherein the polymer composition has low or no significant tack at temperatures below that of skin temperature but which is a pressure sensitive adhesive at skin temperature. The product may be moisture vapor permeable and have a moisture vapor transmission rate of at least 500 g m$^{-2}$ 24 h$^{-1}$ at 37° C. and at a relative humidity difference of 100 to 10%.

10 Claims, No Drawings

ADHESIVE COMPOSITIONS

This application is a continuation of application Ser. No. 08/263,262, filed Jun. 21, 1994 (now abandoned) which was in turn a continuation of Ser. No. 07/924,035, filed as PCT/GB91/00497 Mar. 28, 1991 (now abandoned).

The present invention relates to medical adhesive products such as surgical dressings, surgical drapes, medical tapes and the like and in particular to such products having improved handling and performance characteristics.

Surgical drapes and other adhesive medical products comprising a polyurethane film coated on one surface with a layer of a pressure sensitive adhesive such as a polyvinylether or an acrylic adhesive. Examples of such products include those sold under the Trade Mark 'OpSite' by T. J. Smith and Nephew, Limited. Such products especially the larger size products tend to be difficult to handle because the adhesive tends to stick to itself during application. A product has now been found in which this problem has been alleviated in the form of (a) a substrate, (b) pressure sensitive adhesive on one face of the substrate and (c) a layer on the pressure sensitive adhesive of a composition which has low tack at below skin temperature but which is a pressure sensitive adhesive at skin temperature.

Accordingly the present invention provides a medical adhesive product comprising a substrate, a pressure sensitive adhesive on one face of the substrate and a layer of a polymer composition on the surface of the pressure sensitive adhesive wherein the polymer composition has low or no significant tack at temperatures below that of skin temperature but which is a pressure sensitive adhesive at skin temperature.

Skin temperature is normally in the range 28° C.–35° C. and the adhesive products of this invention will exhibit sufficient tack to adhere to the skin at skin temperatures whilst exhibiting no significant tack at ambient temperature (i.e. 25° C. or less). For the purposes of this document "no significant tack" means that the adhesive in products of the invention will have little or no tendency to stick to themselves at ambient temperature. However when applied to the skin the tack will be sufficient to adhere to the skin within thirty seconds of being applied.

The substrate will suitably comprise a non-woven material, a fibrous material or filmic material. More suitably the substrate will comprise a filmic material with a relatively high moisture vapour permeability.

The substrate of the invention can be any of the substrates used on conventional adhesive dressings. Such substrates include continuous flexible films.

The continuous films for use as a substrate in the invention can suitably have a thickness of 10 to 250 μm more suitably have a thickness of 25 to 35 μm, for example about 30 μm.

Continuous flexible films for the substrate include both moisture vapour permeable and relatively moisture vapour impermeable films. Favoured are continuous moisture vapour permeable films and in particular those films which have a moisture vapour transmission rate of at least 500 g/m²/24 hours at 37° C. at 100% to 10% relative humidity difference (hereinafter g/m²/24 hrs⁻¹) and preferably at least 1000 g/m²/24 hrs⁻¹, for example 1500–2000 g/m²/24 hrs⁻¹. Description 1 provides a method for determining Moisture Vapour Transmission Rate (MVTR).

Such moisture vapour permeable continuous films can advantageously render the adhesive product of the invention permeable to moisture vapour but impermeable to liquid and bacteria.

Apt moisture vapour permeable continuous films include polyester thermoplastic copolymers (for example HYTREL manufactured by the Shell Chemical Company); polyetherpolyamides (for example PEBAX manufactured by ATO Chem) and polyurethanes (for example ESTANE manufactured by Goodrich Chemicals).

Favoured moisture vapour permeable continuous films comprise polyurethane. Suitable polyurethanes include hydrophilic water absorbing polyurethanes such as those disclosed in European Patent Application Nos. 107915 and 0147119, and British Patent No. 1280631, linear polyether and linear polyester polyurethanes such as those known as Estane (available from Goodrich Chemicals) and blends of polyurethane with an incompatible polymer such as those disclosed in European Patent Application No 0046071.

An apt film for use in the invention is a 25 μm thick film of a polyether-polyurethane known as Estane 4714F which film has moisture vapour transmission rate of approximately 1800 g/m²/24 hours at 37° C. at 100% to 0% relative humidity difference.

Favoured relatively moisture vapour impermeable continuous films for use in the invention include films of 1,2-polybutadiene such as those know as RB 810, RB 20 and RB 830 available from Japan Synthetic Rubber Company and films of styrene-butadiene block copolymers including styrene-butadiene-styrene block copolymers such as those know as Kraton or Cariflex available from Shell Chemicals.

An apt continuous film of 1,2 polybutadiene for use in the invention is a 150 μm thick film of RB 830.

An apt continuous film of styrene-butadiene-styrene copolymer is a 30 μm thick film of Kraton 1101.

Suitable pressure sensitive adhesives include any of those normally employed in medical adhesive products. Examples of suitable pressure sensitive adhesives include vinyl ether and acrylic adhesives. More suitably the pressure sensitive adhesive should comprise an acrylic copolymer emulsion such as described in European Patent Application No. 194881 which is herein incorporated by reference. Most suitably the pressure sensitive adhesive will comprise an acrylic ester copolymer as described in European Patent No. 35399 which is herein incorporated by reference.

The pressure sensitive adhesive layer will suitably have a weight per unit area of 10–50 g m⁻², more suitably have a weight per unit area of 20–35 g m⁻² and preferably a weight per unit area of 25–30 g m⁻².

The present invention provides polymers suitable for use as the polymer composition which comprise 60–96% of residues (X), 0–30% of residues (Y) and 0–10% of residues (Z) wherein (X) is an alkyl acrylate or methacrylate wherein the alkyl portions contains 12–20 carbon atoms, (Y) is an alkyl acrylate or methyacrylate wherein the alkyl portion contains 1 to 11 carbon atoms, (Z) is a polar acrylate or methacrylate residue; and wherein the average number of carbon atoms present in (X) and (Y) is at least 12.

In another embodiment the invention provides polymers suitable for use as the polymer composition which polymers suitably comprise 50–96% of residues (X), 1–40% of residues (Y) and 1–10% of residues (z) wherein (X), is an alkyl acrylate or methacrylate wherein the alkyl portion contains 12–20 carbon atoms (Y) is a hydrophilic acrylate or methacrylate ester and (Z) is a polar acrylate or methacrylate residue. Such adhesives form an important aspect of this invention.

The polar acrylate or methacrylate residues may be the acid or an amide thereof or the like. Most suitably Z is acrylic acid or methacrylate acid. Preferably Z is acrylic acid.

Generally the number of different monomers residues X and Y is not more than 4, more suitably not more than 3 and preferably not more than 2. This helps maintain sufficient regularity in the polymer for waxy properties (that is low tack) to be achieved at ambient temperature (eg. at 20° C.).

The residues (X) are more aptly present in excess of 65%. Favourably the residues (X) are unbranched. It is desirable that the alkyl components in X contain 14 to 18 carbon atoms, for example cetyl, lauryl, stearyl or the like residues.

Particularly apt polymers will contain 0–15% of residues (Y). Certain favoured polymer will contain 0–10% of residues (Y). Certain preferred polymers will contain 0% of residues (Y).

Thus certain preferred polymers of this invention will comprise 90–96% of resides (X) and 4–10% of residues (z). In such composition residue Z is preferably the residue of acrylic acid. In such compositions the residues (X) are aptly residues of 2 or 3 different monomers and are most aptly residues of 2 different monomers, for example a stearyl acrylate or methacrylate and a lauryl acrylate or methacrylate.

A particularly preferred polymer of this invention comprises the residues of stearyl methacrylate (47%), lauryl methacrylate (47%) and acrylic acid (6.0%).

The residues (X) are more aptly present in excess of 60%. It is desirable that the alkyl components in X contain 12 to 20 carbon atoms, for example cetyl, lauryl, stearyl or the like residues. The residues (X) can be suitably residues of an alkyl acrylate or methacrylate or combinations thereof which have a straight or branched chain. Favourably the residues (X) are straight. Suitably the alkyl group contains 16 to 20 carbon atoms. The residues (X) can favourably be residues of a straight chain alkyl group containing 16–18 carbon atoms such as cetyl methacrylate. The residues (X) preferably contain straight chain alkyl groups of 18 carbon atoms for example stearyl methacrylate.

The residues (Y) can be residues of a hydrophilic acrylate or methacrylate ester. The residues (Y) will suitably be an alkyl acrylate or methacrylate substituted by one or more hydrophilic groups such as ether groups, amide group, hydroxyl groups, dialkyl amine groups and the like. Aptly the residues (Y) will contain one or more alkoxy groups, for example ether groups.

Aptly the residues (Y) will contain an alkoxy group containing 1–4 carbon atoms. Aptly the alkoxy group will be carried by an alkyl group of 1–6 carbon atoms. Apt alkoxy groups include methoxy, ethoxy, n-propoxy and n-butoxy groups. Apt alkyl groups substituted by such alkyoxy groups include ethyl, n-propyl, n-butyl, isobutyl, sec-butyl and the like.

Other apt residues (Y) will contain a number of —($CH_2CH_2O$)— residues, for example capped polyethylenoxide acrylates or methacrylates such as their monomethyl ethers such as the monomethyl ether of PEG 1000 acrylate.

Particularly apt adhesives will contain 1–40% of residues (Y). Certain favoured adhesives will contain 20–32% of residues (Y). Certain preferred adhesives will contain 26–30% of residues (Y), for example 28%.

Certain preferred adhesives employed in this invention will comprise 60–70% of residues (X) and 4–10% of residues (Z). In such compositions residue Z is preferably the residue of acrylic acid. In such compositions the residues (X) are aptly residues of 2 or 3 different monomers and are most aptly residues of different monomers, for example a stearyl acrylate or methacrylate and a lauryl acrylate or methacrylate.

One favoured adhesive of this invention comprises Stearyl Methacrylate (66%) Butoxyethyl Acrylate (28%) Acrylic Acid (6%).

A further favoured adhesive of this invention comprises Stearyl Methacrylate (66%) Ethyoxyethyl Methacrylate (28%) Acrylic Acid (6%).

A particularly preferred adhesive formulation employed in this invention comprises the residues of stearyl methacrylate (66%), 3 methoxylbutylacrylate (28%) and acrylic acid (6%).

The relative proportions of residues (X), (Y) and (Z) will determine the temperature activated properties of the pressure sensitive adhesive.

The adhesive compositions of the invention can optionally comprise in addition to the copolymer for example fillers or medicaments such as topically effective medicaments which includes chlorhexidine and its salts, cetrimide and silver sulphadiazine.

The polymer which comprises the coating of the pressure sensitive adhesive layer will suitably have a weight per unit area of 1–20 $gm^{-2}$ more suitably it will have a weight per unit area of 3–10 $gm^{-2}$ and preferably a weight per unit area of 4–8 $gm^{-2}$, for example 5, 6 or 7 $gm^{-2}$. The thickness and continuity of the coating for the pressure sensitive adhesive layer should be sufficient to block the pressure sensitive adhesive layer at below skin temperature whilst simultaneously being of sufficient thickness to exhibit its pressure sensitive adhesive properties within a few seconds of being applied to the skin.

The polymer coating of the pressure sensitive adhesive layer should suitably have no significant tack at a temperature of less than 20° C., more suitably it should have no tack at a temperature of less than 22° C. and preferably it should have no tack at a temperature of less than 25° C. More preferably it should have no significant tack at a temperature of less than 28° C. At temperatures above 28° C. the polymer coating should preferably have sufficient tack thereby enabling the coating to assume the properties of the pressure sensitive adhesive layer at skin temperature which is normally in the range of 28°–35° C. The MVTR of the adhesive layer together with the polymer coating will aptly be at least 500 $gm^{-2}$ and more aptly at least 750 g $m^{-2}$ 24 hr at 37° C. and at a relative humidity. In practical terms the MVTR of the adhesive layer together with the polymer coating will be determined by its thickness and will rarely exceed 2000 $gm^{-2}$.

The MVTR of the completed product can be determined using the Payne Cup method as described in Description 1 at 37° C. with a relative humidity difference of 100–10%. The MVTR of the completed product will favourably be at least 350 $gm^{-2}$ 24 $hrs^{-1}$, more suitably at least 500 $gm^{-2}$ and preferably at least 650 $gm^{-2}$.

In order to determine the MVTR of the backing layer by this method it is preferably to determine the MVTR of the substrate prior to adhesive coating. Alternatively the adhesive layer can be removed from the substrate of the completed device in any convenient manner for example by cryogenic separation or solvent dissolution.

The MVTR of the adhesive layer together with the polymer coating is obtained mathematically by measuring the MVTR of the completed product and of the substrate alone and employing the formula $d^{-1}=b^{-1}+a^{-1}+c^{-1}$ where d is the MVTR of the completed product, b is the MVTR of the substrate and a is the MVTR of the pressure sensitive adhesive layer, and c is the MVTR of the polymer coating.

From the previous disclosure it will be realised that in one embodiment the device of the invention provides for a medical adhesive product consisting essentially of the named layers. Such medical adhesive products include surgical drapes, surgical dressings, first-aid dressings, medical tapes for attachment of dressing or other items to the body, ostomy products and incontinence products.

For use as a surgical drape or surgical dressing the area of the device of the invention can be any suitable size for application to the body. For use as a surgical drape or surgical dressing such areas could be up to 84 cm×56 cm, for example 45 cm×55 cm, 45 cm×28 cm, 20 cm×28 cm, 15 cm×20 cm, 15 cm×10 cm, 10 cm×10 cm or 5 cm×7 cm.

A surgical drape or surgical dressing as previously described can be applied to the skin by any suitable method. Particularly favoured forms of presentation are those described in European Patent Specification Nos. 161865 and 341045 which are herein incorporate by reference.

Surgical drapes and surgical dressing of the device of the invention can be applied without wrinkles, folds and channels being formed. The heat insulation provided by surgeons gloves allow the drapes or dressings coated with the waxy polymer to be handled easily allowing unhurried and methodical attachment by means of a gentle smoothing action. Contact with skin for a few second allows the polymer to melt and assume the properties of the pressure sensitive adhesive which adheres to the skin in the normal way. This property of the device of the invention offers particular advantages for large surgical drapes which are notoriously difficult to handle. It also offer economical advantages in that it reduces waste caused by application failure.

In a further embodiment the device of the invention can be a first-aid dressing of any suitable size or form for such dressings. For example as a strip as a fingertip dressing, as an anchor dressing or as an eye occlusion patch. Sizes of such products could be for example 3.8 cm×2.2 cm, 7.5 cm×3.7 cm or 7.5 cm×5 cm in a further embodiment the device of the invention can be a medical tape in the form of a roll of varying width and length for example from 1.25 cm×10 m to 30 cm×10 m. In a further embodiment the device of the invention can be a product for ostomy care in the form of an adhesive face plate attached to which would be a gasket and the ostomy pouch. In a further embodiment the device of the invention can be a product for incontinence care in the form of an adhesive face plate to which the incontinence device could then be attached.

The resultant product can be provided on a bacteria proof pouch and sterilised by a convenient method such as gamma irradiation or ethylene oxide.

The invention will now be illustrated by reference to the following examples.

EXAMPLE 1

A mixture of stearyl methacrylate (65.8 g) 2-ethylhexyl acrylate (28.2 g) and acrylic acid (6 g) monomers and a solution of catalyst BCHPC (0.2 g) in ethyl acetate (100 g) was slowly added by means of dropper funnels to ethyl acetate (50 g) heated under reflux (80° C.) in a resin flask over a period of approximately 6 hours. Further ethyl acetate (50 g) was added to the mixture during the polymerisation to maintain the mixture in a viscous by ungelled state.

The resultant solution contained 33% by weight of the copolymer. The alkyl groups of the residues in the copolymer had an average of 13 carbon atoms.

The resulting adhesive coating was then applied at a weight per unit area of 7 gm$^2$ to a polyurethane film (30 gsm of Estane 1417) which had previously been coated on one surface with an acrylate ester copolymer pressure sensitive adhesive (PSA) at a weight per unit area of 30 gm$^{-2}$. The coating was applied to the layer of the film on which contained the coating of the acrylate ester copolymer PSA. The adhesive coating was pressure sensitive at 28° C. which enabled dressings or drapes (10×10 cm and 20×40 cm) made from the coated film to be applied easily to the skin.

The MVTR of the completed product was found to be 525 gm$^{-2}$ 24 hrs$^{-1}$.

EXAMPLES 2–7

The following adhesives were prepared by the method of Example 1:

| Example | 2 | 3 | 4 | 5 | 6 | 7 |
|---|---|---|---|---|---|---|
| Stearyl Methacrylate | 47 | 66 | 84.6 | 80 | 75.5 | 66 |
| Lauryl Acrylate | 47 | — | — | — | — | — |
| 2 Ethylhexyl Acrylate | — | 28 | 9.4 | 14 | 4.7 | 28 |
| Acrylic Acid | 6 | 6 | 6 | 6 | — | — |
| Methyl Methacrylate | — | — | — | — | 19.8 | — |
| Acrylamide | — | — | — | — | — | 6 |

The adhesive of Example 2 was particularly good exhibiting no significant tack at about 20° C. but showing good pressure sensitive adhesive properties at 30° C.

Surgical drapes made as described in Example 1 employing the polymer of Example 2 were able to be applied without wrinkling, folds or channels being formed. The heat insulation provided by surgeons' gloves allow the drapes coated with the waxy polymer to be handled easily allowing unhurried and methodical attachment by means of a gentle smoothing action. Contact with the skin for a few seconds allowed melting of the polymer which then assumes pressure sensitive adhesive properties which adhere to the skin in the normal way.

EXAMPLES 8–9

A mixture of stearyl methacrylate (65.8 g) 3-methoxybutylacrylate (28.2 g) and acrylic acid (6 g) monomers and a solution of catalyst BCHPC (0.2 g) in ethyl acetate (100 g) was slowly added by means of dropper funnels to ethyl acetate (50 g) heated under reflux (80° C.) in a resin flask over a period of approximately 6 hours. Further ethyl acetate (50 g) was added to the mixture during the polymerisation to maintain the mixture in a viscous by ungelled state.

The resultant solution contained 24% by weight of the copolymer.

The copolymer solution was applied at a weight per unit area of 7 gm$^{-2}$ to a polyurethane film (30 gm$^{-2}$ of Estane 5714F) which had previously been coated on one surface with an acrylate ester copolymer pressure sensitive adhesive (PSA) at a weight per unit area of 30 gm$^{-2}$. The coating of the polymer was applied to the layer of the film which contained the coating of the acrylate ester copolymer PSA.

The adhesive coating was found to be non-tacky at 20° C. but to be tacky and pressure sensitive at 28° C. which enable dressings (10 cm×10 cm) or drapes (20 cm×40 cm) made from the coated film to be applied easily to the skin without wrinkling or folding.

The MVTR of the completed product was found to be 677 gm$^{-2}$ 24 hrs$^{-1}$.

The heat insulation provided by a surgeons gloves allowed the drapes coated with the waxy polymer to be handled easily allowing unhurried and methodical attachment by means of a gentle smoothing action. Contact with the skin for a few seconds allowed melting of the polymer which then assumes pressure sensitive adhesive properties which adhere to the skin in the normal way.

EXAMPLE 9

Example 8 was repeated but the adhesive was prepared by substituting ethyl acetate for acetone in the same proportions. The reflux temperature was 60° C. and was carried out for approximately 12 hours.

Description 1

The Payne Cup Method of MVTR Determination

Discs of the material under test are clamped over Payne Permeability Cups (flanged metal cups) using sealing rings and screw clamps. The flanges on the cups are previously coated with an acrylic adhesive to a weight per unit area of 30 gm$^{-2}$. The exposed surface area of the test sample is 10 cm$^2$. Each cup contains approximately 10 ml of distilled water.

After weighing the cups are placed in a fan assisted oven which is maintained at 37°±1° C. The relative humidity within the oven is maintained at approximately 10% by placing 1 kg of anhydrous 3-8 mesh calcium chloride on the floor of the oven.

The cups are removed after 24 hours, allowed to cool for 20 minutes and re-weight. The MVP of the test material is calculated from the weight loss and expressed in units of grams of weight per square meter per 24 hours.

I claim:

1. A medical adhesive product comprising a substrate, a pressure sensitive adhesive on one face of the substrate and a layer of a polymer composition on the surface of the pressure sensitive adhesive wherein said polymer composition has low or no significant tack at temperatures below that of skin temperature but which is a second pressure sensitive adhesive at skin temperature and wherein said polymer composition comprises 50–96% of residues (X), 1–40% of residues (Y) and 1–10 of residues (Z) wherein (X) is an alkyl acrylate or methacrylate having an alkyl portion containing 12–20 carbon atoms, (Y) is a hydrophilic acrylate or methacrylate ester containing an alkoxy group containing 1–4 carbon atoms; and (Z) is a polar acrylate or methacrylate residue.

2. A product according to claim 1, wherein said alkoxy group of residues (Y) is carried by an alkyl group of 1–6 carbon atoms.

3. A product according to claim 2 wherein said alkyl group is selected from the group consisting of ethyl, n-propyl, n-butyl, isobutyl and sec-butyl.

4. A product according to claim 1 wherein said alkoxy group is selected from the group consisting of methoxy, ethoxy, n-propoxy and n-butoxy.

5. A product according to claim 1 in which the polymer composition comprises about 66% stearyl methacrylate residues, about 28% 3-methoxybutylacrylate residues and about 6% acrylic acid residues.

6. A product according to claim 1 which is moisture vapor permeable and has a moisture vapor transmission rate of at least 500 g m$^2$ 24 hr$^{-1}$ at 37° C. and at a relative humidity difference of 100 to 10%.

7. A product according claim 1 in which said substrate is comprised of one of a continuous polymeric film, an apertured polymeric film, a knitted fabric or a woven or non-woven fabric.

8. A product according to claim 1 in which said polymer composition additionally comprises a filler.

9. A product according to claim 1 in which said polymer composition additionally comprises a topically effective medicament.

10. A product according to claim 1 in the form of one of a wound dressing, a surgical drape or an applicator for an ostomy device.

* * * * *